United States Patent
Danielson

(10) Patent No.: US 10,368,650 B2
(45) Date of Patent: Aug. 6, 2019

(54) ERGONOMIC CHAIR MADE FROM PAPER SUBSTRATE WITH EMBEDDED SENSOR, COMPUTER READABLE MEDIUM FOR INTERACTING WITH THE CHAIR, METHOD OF MAKING THE CHAIR OR OTHER STRUCTURES FROM PAPER SUBSTRATE

(71) Applicant: Patrick Allen Danielson, Sudbury (CA)

(72) Inventor: Patrick Allen Danielson, Sudbury (CA)

( * ) Notice: Subject to any disclaimer, the term of this patent is extended or adjusted under 35 U.S.C. 154(b) by 125 days.

(21) Appl. No.: 15/498,069

(22) Filed: Apr. 26, 2017

(65) Prior Publication Data
US 2017/0311726 A1 Nov. 2, 2017

Related U.S. Application Data

(60) Provisional application No. 62/328,230, filed on Apr. 27, 2016.

(51) Int. Cl.
*A47C 5/00* (2006.01)
*A47C 9/00* (2006.01)
(Continued)

(52) U.S. Cl.
CPC ............... *A47C 9/002* (2013.01); *A47C 3/029* (2013.01); *A47C 5/005* (2013.01); *A47C 7/72* (2013.01);
(Continued)

(58) Field of Classification Search
CPC ......... A47C 9/002; A47C 3/029; A47C 5/005; A47C 7/72; A47C 15/004; A61B 5/1116;
(Continued)

(56) References Cited

U.S. PATENT DOCUMENTS

| 7,478,878 B2 * | 1/2009 | Oettinger | A47C 3/029 297/271.5 |
| 8,403,422 B2 * | 3/2013 | Wu | A47C 7/02 297/440.12 |

(Continued)

FOREIGN PATENT DOCUMENTS

| DE | 202005005300 | 5/2005 |
| GB | 1215475 | 12/1970 |

OTHER PUBLICATIONS

Communication from European Patent Office, including Partial European Search Report for European Patent Application No. 17168362.6, dated Sep. 25, 2017 (13 pages).

*Primary Examiner* — Syed A Islam
(74) *Attorney, Agent, or Firm* — McCracken & Gillen LLC

(57) ABSTRACT

There is provided an ergonomic chair which is produced from flat components. The components may be made of paper. The components are designed using parametric equations which take the targeted user's proportions into account. The components are then folded, joined, and coated with strengthening material. The chair has a seat, a base, and three legs connecting the seat to the base. The base contains a counterweight mass for keeping the chair in a default upright position. The base contains an accelerometer which can transmit data to a computing device to track a user's posture and other health-related data.

15 Claims, 25 Drawing Sheets

(51) Int. Cl.

| | |
|---|---|
| *A47C 3/029* | (2006.01) |
| *A47C 15/00* | (2006.01) |
| *A61B 5/11* | (2006.01) |
| *A61B 5/00* | (2006.01) |
| *A47C 7/72* | (2006.01) |

(52) U.S. Cl.
CPC .......... *A47C 15/004* (2013.01); *A61B 5/1116* (2013.01); *A61B 5/1118* (2013.01); *A61B 5/4519* (2013.01); *A61B 5/4528* (2013.01); *A61B 5/486* (2013.01); *A61B 5/6891* (2013.01); *A61B 5/742* (2013.01); *A61B 5/7455* (2013.01); *A61B 2562/0219* (2013.01)

(58) Field of Classification Search
CPC ... A61B 5/1118; A61B 5/4519; A61B 5/4528; A61B 5/486; A61B 5/6891; A61B 5/472; A61B 5/7455
USPC .................................................... 297/440.12
See application file for complete search history.

(56) References Cited

U.S. PATENT DOCUMENTS

| | | | |
|---|---|---|---|
| 2011/0215631 A1 | 9/2011 | Wu | |
| 2016/0081483 A1* | 3/2016 | Harrison | A47C 31/126 297/217.2 |
| 2016/0195923 A1* | 7/2016 | Nauseef | G06F 3/012 348/121 |

* cited by examiner

FIG. 43
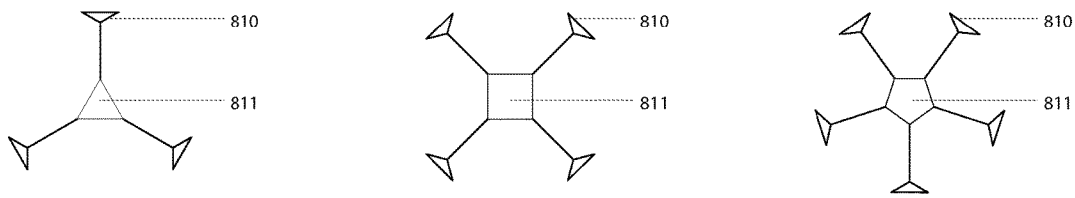
FIG. 44
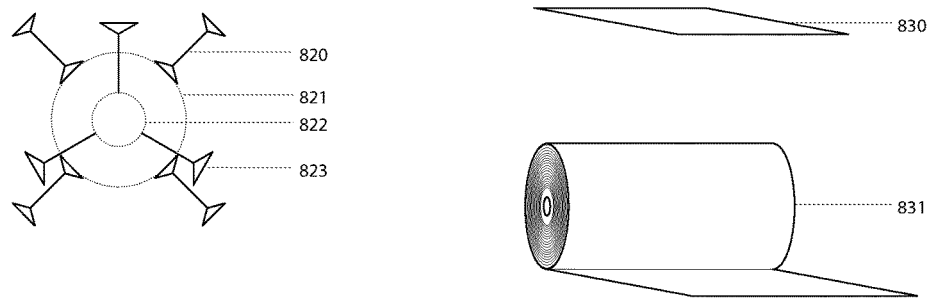
FIG. 45
FIG. 46
FIG. 47
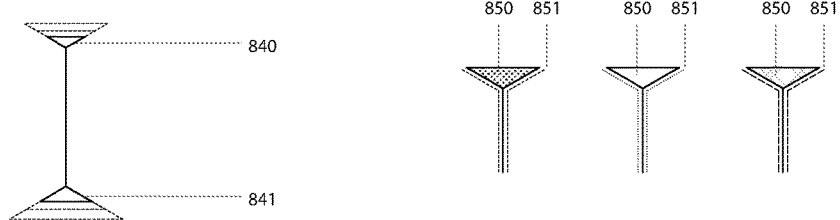

ERGONOMIC CHAIR MADE FROM PAPER SUBSTRATE WITH EMBEDDED SENSOR, COMPUTER READABLE MEDIUM FOR INTERACTING WITH THE CHAIR, METHOD OF MAKING THE CHAIR OR OTHER STRUCTURES FROM PAPER SUBSTRATE

CROSS REFERENCE TO RELATED APPLICATIONS

The present application claims benefit of Danielson, U.S. Provisional Patent Application No. 62/328,230, filed Apr. 27, 2016. The entire contents of this application are incorporated herein by reference.

TECHNICAL FIELD

The present invention relates generally to structures made from paper substrate such as chairs and, more particularly, to ergonomic chairs having embedded sensors to provide feedback to the user via a software application.

BACKGROUND

Various designs for active ergonomic chairs are known in the art. For example, the use of a free-standing exercise ball as a seat surface has become a common practice in the workplace. A kinetic supporting surface will activate muscles and produce a positive physiological response whether the ball is in a static position or moving in multi-directional ranges. However, exercise balls are limited in terms of postural accuracy, formality, and safety. They also cannot be used for convenient digital data acquisition. Due to the inflatable nature of the exercise ball, it cannot maintain the precise, ergonomic optical relationships between the body and other seating environment elements. Also, the lack of a discernible "up" orientation and the flexibility of the ball material make it difficult to record a user's posture with a digital device.

Another example of an ergonomic seating system is the Focal Mogo Seat, which comprises a seat attached to a shaft which forms the base and allows a user to sit upright and provides a better relationship between the user's spine and legs. However, the sitting position required by such a seat results in misaligned ankles which cannot be maintained indefinitely without adverse effects on the user. Moreover, this type of seat cannot independently support itself and therefore falls down every time the user lets go of it.

Balance ball chairs, such as those produced by Gaiam, are a hybrid between an exercise ball and traditional chair with a raised outer shell for the exercise ball. This reduces the radius of the ball and provides mobility on the floor through wheels. This allows the users to position themselves at a precise height with a back rest. However, the plastic materials used are all less renewable, the product is not adjustable, and it cannot be tailored (i.e. customized) to an individual user's dimensions. Moreover, the exercise ball would slowly deflate with use, causing a need for constant upkeep. The primary advantage of sitting on an exercise ball on its own (the ability to move the ball in multiple directions and generate active balance while seated) is also negated in balance ball chairs, and the ball is effectively reduced to an air cushion.

Ergonomic knee chairs are also known in the art. These seats improve the angle between the legs and back in order to set up an improved spinal curvature. However, the configuration of these seats is damaging to the knee joints and requires somewhat awkward entry into and exiting from the seat, thus reducing the ease of use.

Rocking stools are also known in the art, such as those produced by Monarchy. These designs are a more formal version of the classic exercise ball, and use rigid wood with curved arches contacting the ground. However, certain limitations of this design prevent prolonged use. First, the posture required for the rocking stools low setting and the lack of options for adjustability in conjunction with the flat hard seat surface will cause lower back fatigue and discomfort for the user. The underside of the rocking surface of the wooden stool may also cause slipping if too extreme an angle is assumed by the user. Since it is not a counterweight design, more space is taken up at the base by a wider supporting structure.

Most adjustable chairs known in the art will require a certain degree of maintenance and repair. For example, bolts and screws may loosen or fall out. Hydraulic cylinders can fail to hold, or seize. Hair and lint can get stuck in casters, causing issues with rolling.

Most ergonomic chairs are designed to increase comfort by maximizing adjustability and support. However, increased comfort while sitting reduces both physical and mental awareness of the body and such chairs do not prompt the user to move. Ultimately, both the physical and mental effort required from the user while sitting are significantly reduced.

There are at least three problems with this focus. First, when one is sitting for hours at a desk the body needs to be moving frequently in order to reduce the negative health outcomes associated with prolonged sitting. It is essential to remain active, and this problem isn't solved merely by changing the user's body position from one prolonged static position into another prolonged static position. Second, when chairs reduce the effort required to sit for prolonged periods, the capacity for activity is reduced and the user becomes increasingly dependent on support from such comfort giving chairs. Thirdly, there is no opportunity for the user to gain awareness of their posture and body position through self-monitoring and feedback. Additionally, many existing ergonomic chairs can be adjusted to accommodate the user's unique needs. However, depending on the training of the "adjuster," adjustments may not be appropriate to meet unique long term needs and can actually end up causing more harm than good.

It would be desirable to have a chair with few maintenance issues, and no redundant moving parts and whose movement does not depend on mechanical parts. It would be further desirable to achieve a less constrained range of movement, wherein the centre of gravity for both the body and the seat can be aligned. It would also be desirable to reduce production costs while still allowing for customization (tailoring) for individuals. It would also be desirable to record and obtain statistics regarding orthopedic status of the user of such ergonomic devices from data relating to the user's posture and overall health. It would be desirable to utilize technology to increase the user's body awareness through feedback and self-monitoring with the ultimate goal of self-management where the user will be able to carry over gained knowledge to other contexts (without the use of technology) whether it be other sitting surfaces or other positions.

SUMMARY

The following presents a simplified summary of some aspects or embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

One aspect of the invention is a chair that includes a base including a counterweight, a seat connected to the base and supported above the base by a seat-supporting structure, and wherein each of the base, the seat and the seat-supporting structure are made at least in part of folded paper substrate material.

Another aspect of the invention is a chair having a base including a counterweight, a seat connected to the base and supported above the base by a seat-supporting structure, and a single accelerometer for providing position data. The chair also includes a wireless transceiver for communicating wirelessly with a computing device and for transmitting the position data to the computing device.

Another aspect of the invention is a computer-readable medium comprising computer-readable instructions in code which, when stored in a memory of a computing device and executed by a processor of the computing device, cause the computing device to receive accelerometer data from an accelerometer in a chair, process the data and display information on a display of the computing device relating to a seating position of a user.

Another aspect of the invention is a method of making a chair, the method comprising providing a flat paper substrate material, folding the paper substrate material to form components of the chair and joining the components of the chair to form the chair.

Another aspect of the invention is a method of making a paper-based structure, the method comprising providing a flat paper substrate material, folding the paper substrate material to form components of the structure and joining the components of the chair to form the structure.

Another aspect of the invention is a structure made according to the foregoing method.

BRIEF DESCRIPTION OF THE DRAWINGS

Further embodiments and details of the present invention are described in further detail below in conjunction with the drawings, in which.

Figure 33:
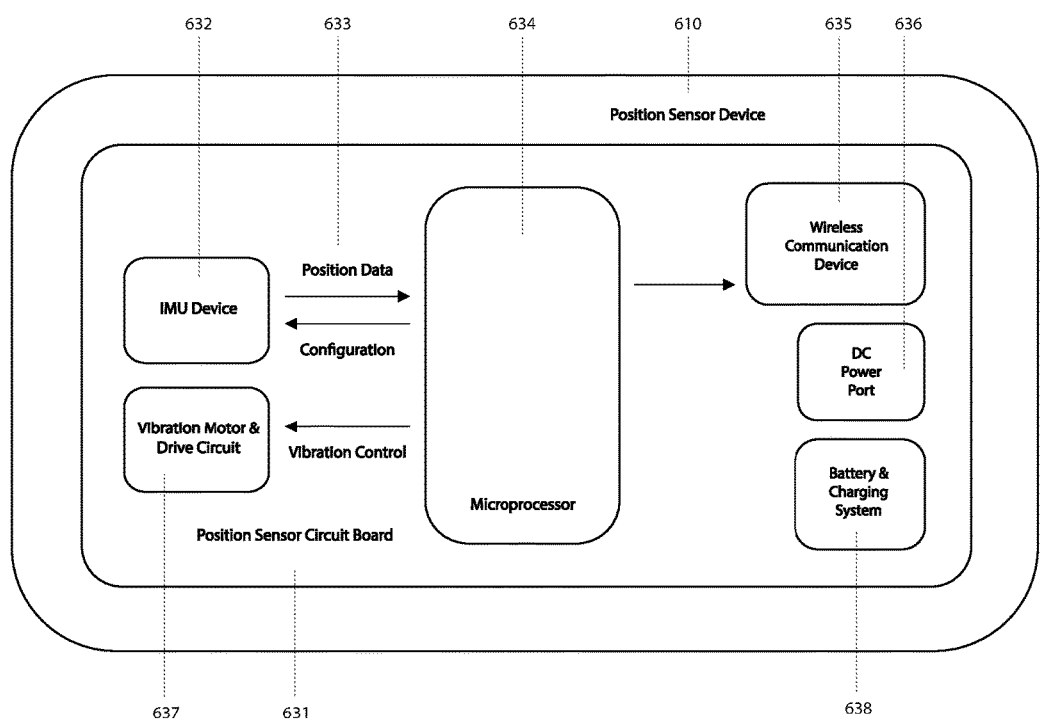

In the embodiment illustrated in FIG. 33, the inertial measurement unit (IMU) device 632 includes an accelerometer. Configuration data is passed from the microprocessor 634 to the IMU device 632 for calibration and initialization parameters. The microprocessor 634 controls the vibration movements. The circuit board assembly will contain a wireless communication device 635, and a battery and charging system 638. In the embodiment illustrated in FIG. 33, a direct current (DC) power port 636 is used for battery charging only.

Figure 34:
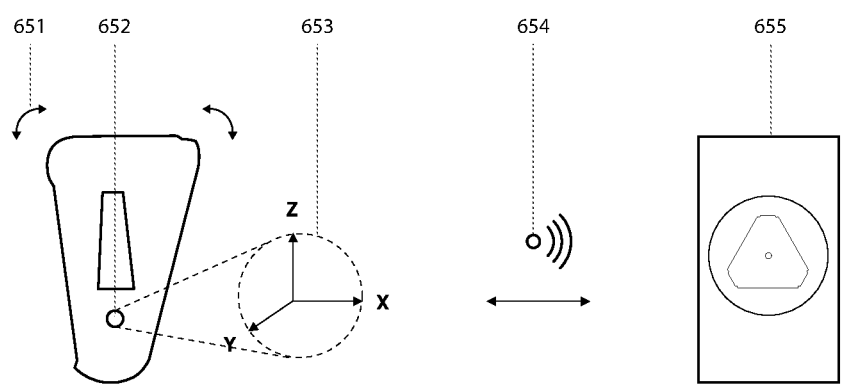

FIG. 34 illustrates the orientation of axes for the position data that are used to activate a wireless data connection with a computing device.

FIGS. 35-40 are illustrations of various graphical user interfaces of an application running on a computing device which receives data from an accelerometer.

Figure 41:
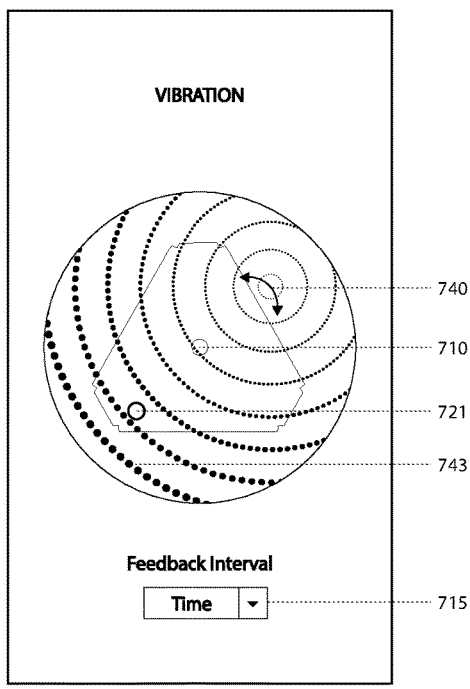

FIG. 41 illustrates a graphical user interface of an application running on a computing device which sends data to the vibration motor and drive circuit as feedback.

Figure 42:
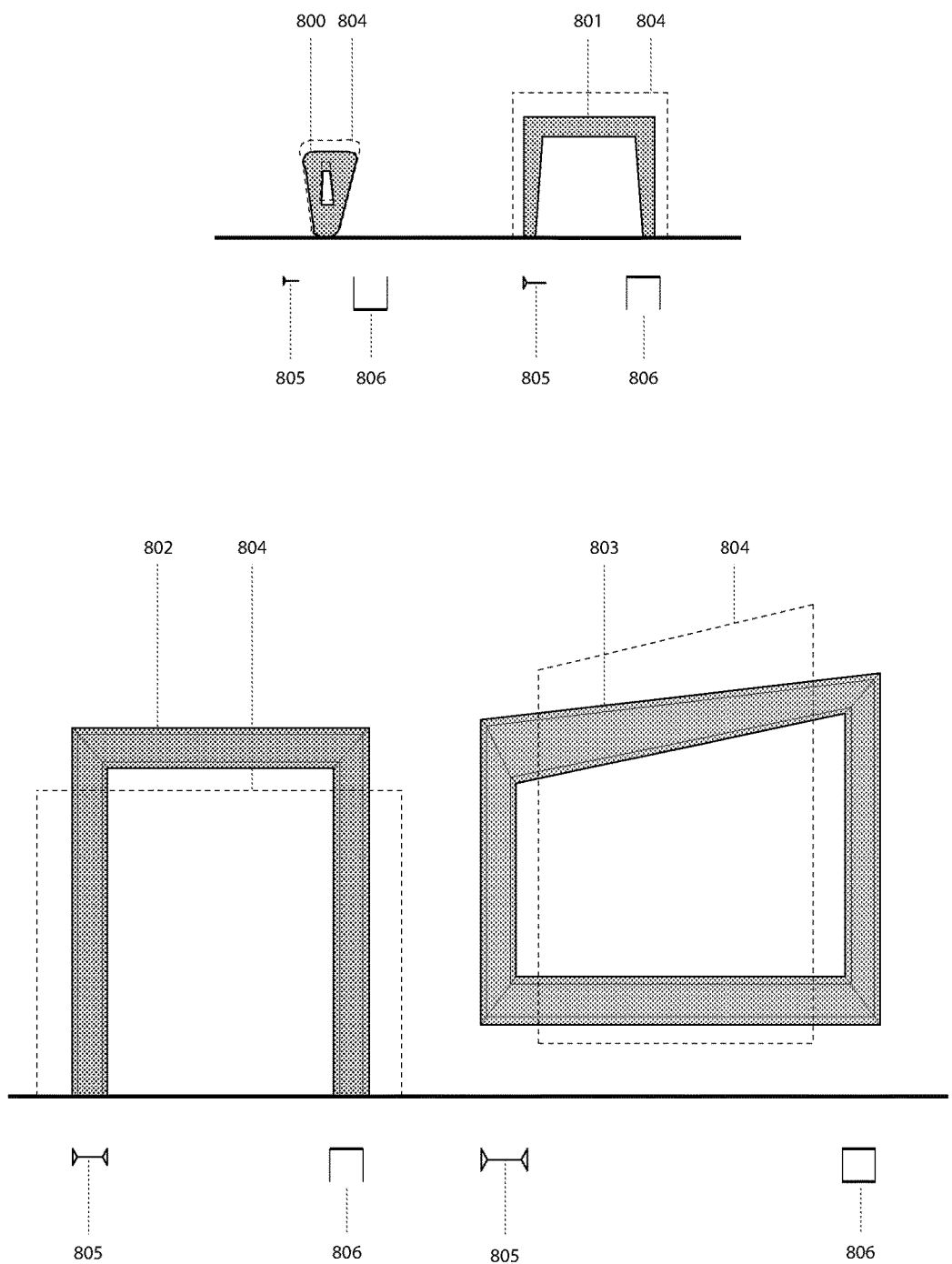

FIG. 42 shows the scalability of this invention to larger scales including architecture.

FIGS. 43-47 illustrate methods to achieve scaled up embodiments of the present invention in which additional members are used, stronger moment of inertia shapes are used, larger stock material options are pursued, independently controlled ends and material selection also affect the overall dimensions.

FIGS. 1-47 include reference numerals 100s-800s that refer to components, parts, elements, movements, configurations and other details. The reference numerals in the 100s denote finished product configurations, whereas the reference numerals in the 200s denote movement. the 300s denote the component assembly sequence, the 400s denote the component configurations, the 500s denote the tailored methodology, the 600s denote the electronics, the 700s denote the digital feedback, and the 800s denote the alternative configurations, materials, and scale using the same construction process.

DETAILED DESCRIPTION

The following detailed description contains, for the purposes of explanation, numerous specific embodiments, implementations, examples and details in order to provide a thorough understanding of the invention. It is apparent, however, that the embodiments may be practiced without these specific details or with an equivalent arrangement. In other instances, some well-known structures and devices are shown in block diagram form in order to avoid unnecessarily obscuring the embodiments of the invention. The description should in no way be limited to the illustrative implementations, drawings, and techniques illustrated below, including the exemplary designs and implementations illustrated and described herein, but may be modified within the scope of the appended claims along with their full scope of equivalents.

100s, 300s, 400s (Basics, Parts, Assembly)
Basic Description

Some embodiments of the present invention relate to a user-stabilized chair built from a folded paper substrate, and customized for each individual user for ergonomic alignment and activity. Further embodiments relate to an ergonomically correct, tailored active seating device, for example, a chair. The components of a chair according to an example embodiment of the invention is shown in FIGS. 1-8. In the embodiment depicted in FIGS. 1-8, the chair 100 comprises a base 101, three leg portions 102 defining a seat-supporting structure, and a seat or seat portion 103. The base 101 comprises a counterweight mass 134 (also referred to herein simply as a "counterweight") which operates to bias the chair in an upright position by default, as the centre of mass of the chair would be located very close to the bottom of the base. The chair optionally further comprises a seat top cushion 131 containing, for example, a high-density foam. The chair may also include express printed graphics on the folded paper elements 150.

Paper and Counterweight

According to some embodiments, the use of paper substrates for a counterweight design is important because the entire chair or product becomes lighter than comparable products. Moreover, in the embodiment depicted in FIGS. 1-8, the pulp mass 133 in the legs may be distributed to the periphery, which may allow the central volume to be more or less free of material. Similar to an I-beam, where most of the mass would be expressed on the outer perimeter, a similar result may be achieved by setting up the folded formwork 135 to build mass away from the center. This arrangement can improve or even maximize the moment of inertia, which means that less material is required for vertical support. Due to this lowered structural demand, in some embodiments the paper substrates are more easily accommodated. Other designs which support a user's weight directly underneath the middle of the seat or chair would not be as effective or conducive to using paper substrates as the building material.

No Moving Parts

By using fixed and rigid construction, it is possible in some embodiments to achieve improved durability of materials, reliability of movement and aesthetic simplicity.

Pressure

In some embodiments, as shown for example in FIGS. 1-8, the triangular shape of the seat 103 in plan view will cause the user's coccyx to be free of encountering any abrupt pressure. Further, the pressure points in the seat cushion 131 may be limited by the use of high density foam and maximized surface area contact between the seat and the user's body. The open space underneath the seat 103 provides additional pressure relief for the user.

Ventilation & Foam

In some embodiments, the seat cushion 131 of the seat 103 is made of high density foam, which facilitates maximizing the surface area contact between the seat and the body contour for healthier pressure distribution and comfort. Fabrics which retain allergens and dust may be avoided in some embodiments. Materials such as vinyl, which cause the user to sweat, may also be avoided in some embodiments. In FIGS. 1-9 seat 103 may be made of a tensile material that spans between the foam seat edges, connected at the corners 136 and contains a few holes 130 centrally located above the paper tube void 410 for both ventilation and a lifting function.

Sustainable

As noted above, in some embodiments, the components of the chair 100 are made from paper substrate materials. Paper substrates may offer a number of advantages over other building materials, namely: carbon sequestration, recyclability, and a reduction in the overall material weight of the chair. This reduced overall weight reduces the mass required in the base 101 to act as a counterweight 134 for the chair 100. More broadly, the use of paper substrates also supports the cultivation of medium growth forests, which leads to a more sustainable harvesting strategy. Furthermore, waste from various processes may be embedded in the counterweight mass 134 in or on the base 101 of the chair 100, which mitigates harmful environmental effects while also reducing the need for consumption of additional material for the counterweight mass 134. The reduced weight would also result in lower transportation costs per unit compared to heavier materials.

Flat to 3D

According to one aspect of the present invention, the individual components of the chair 100 may be produced as flat paper stock or substrate, which are subsequently folded at precise points 336 to assume a three-dimensional shape. FIGS. 13-16 illustrate overhead views of the initially produced flat forms, including fold lines, of the seat 301, leg 302, base 303, and cushion 304.

Fold Sequence

Figure 17:
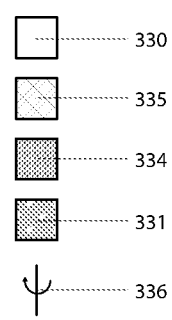
FIG. 17 illustrates the hatch coding for FIGS. 13A-16.
Figure 18A:
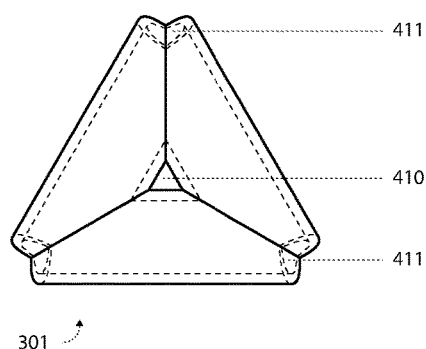
FIGS. 18A-18D show top, back, side and perspective views of example embodiments of tube seat components of the chair when assembled.
Figure 18B:
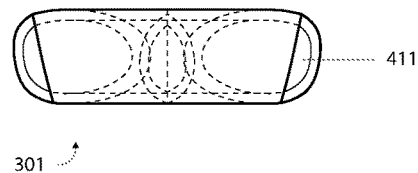
Figure 18C:
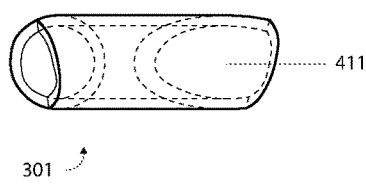
Figure 18D:
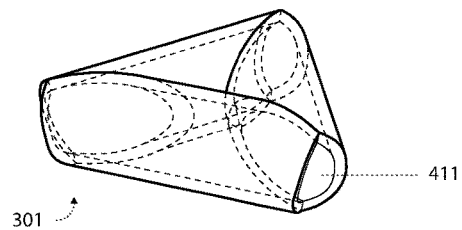
Figure 19A:
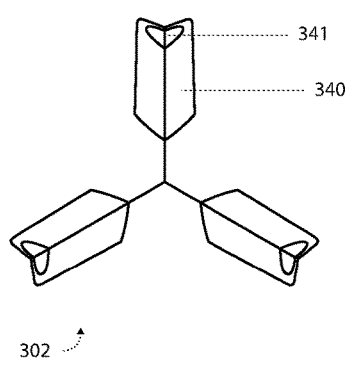
FIGS. 19A-19D show top, back, side and perspective views of example embodiments of folded leg components of the chair when assembled.
Figure 19B:
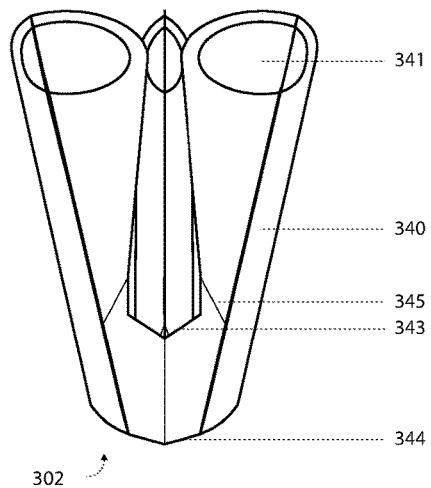
Figure 19C:
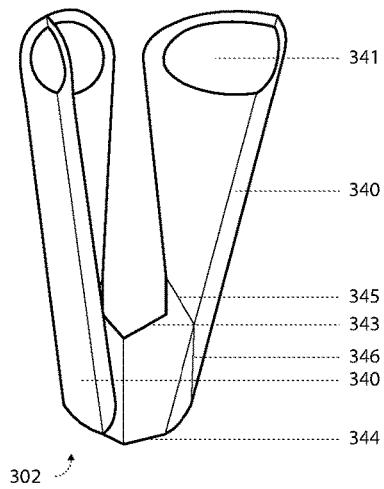
Figure 19D:
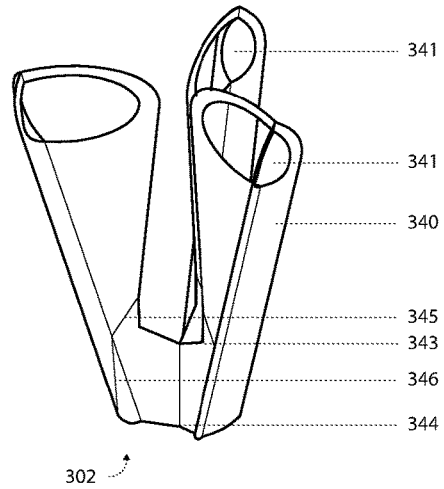
Figure 20A:
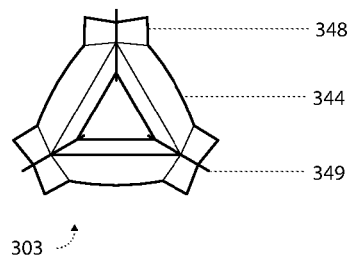
FIGS. 20A-20D show top, back, side and perspective views of example embodiments of folded base components of the chair when assembled.
Figure 20B:
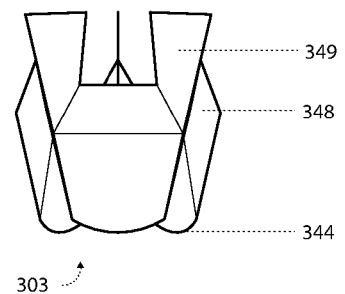
Figure 20C:
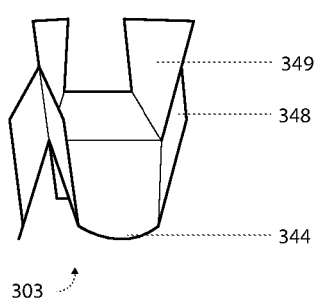
Figure 20D:
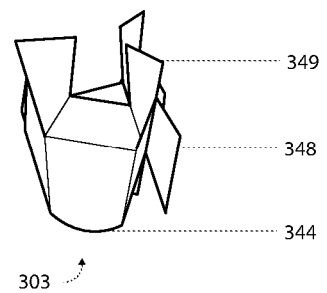
Figure 21A:
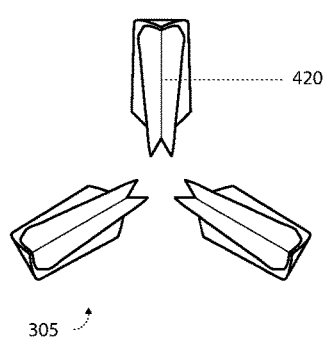
FIGS. 21A-21D show top, back, side and perspective views of example embodiments of cast pulp mixture components of the chair when assembled.
Figure 21B:
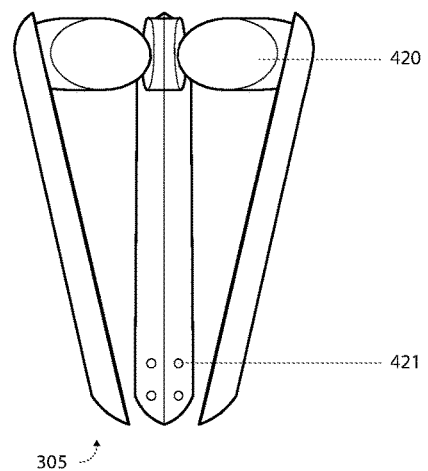
Figure 21C:
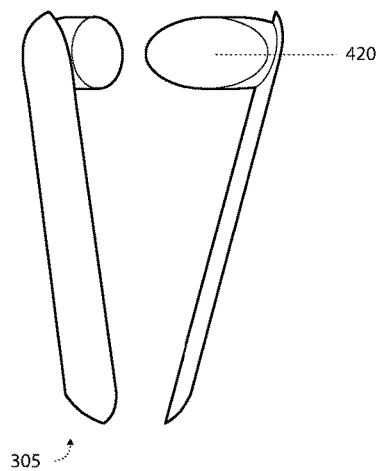
Figure 21D:
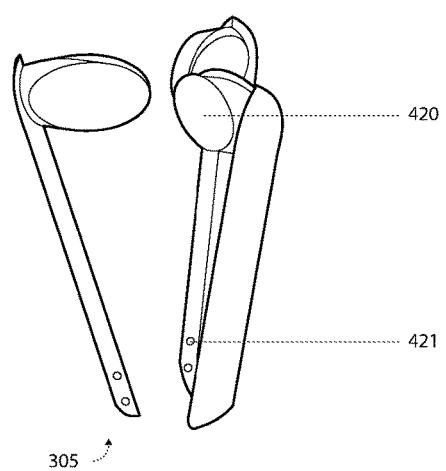
Figure 22A:
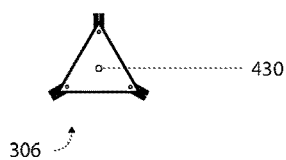
FIGS. 22A-22D show top, back, side and perspective views of example embodiments of digital housing components of the chair when assembled.
Figure 22B:
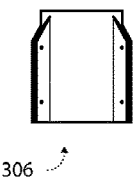
Figure 22C:
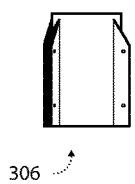
Figure 22D:
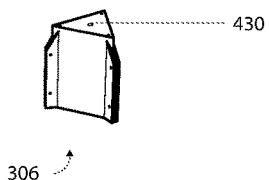
Figure 23A:
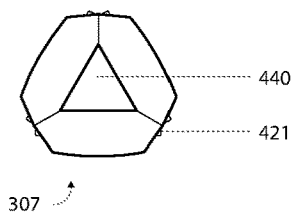
FIGS. 23A-23D show top, back, side and perspective views of example embodiments of cast counterweight components of the chair when assembled.
Figure 23B:
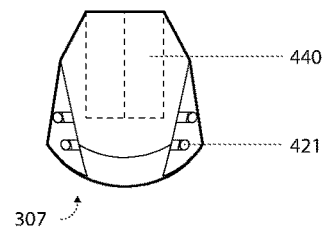
Figure 23C:
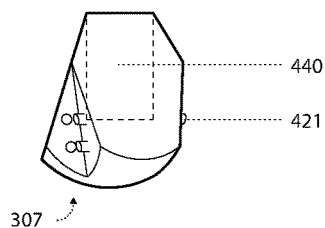
Figure 23D:
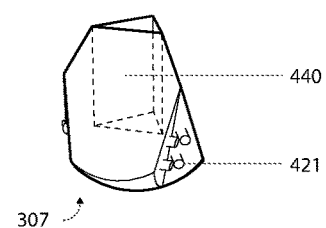

A general overview of the assembly process is shown in FIGS. 13-16. In some embodiments, the assembly process begins with the production of the flat paper stock. The flat paper is then machine cut and scored into the foldable component 330 with graphics printed on the flat paper 334 by, for example, a digital die cutter and the leftover paper 331 can be reused. In relation to the initially flat components in FIG. 13A-13E, they show a step-by-step illustration of how an example embodiment of seat 301 begins as flat paper 330 and is wrapped onto a paper tube 333 to produce a three-dimensional component where the edges 332 mark the straight cut boundary. Likewise, FIGS. 14A-14F show a step-by-step illustration of how an example embodiment of leg 302 is folded into an assembled, three-dimensional component showing the front 330 & 334 and back 335 sides of the folded elements. Finally, FIGS. 15A-15G show a step-by-step illustration of how an example embodiment of base 303 is folded into an assembled, three-dimensional component. FIG. 17 shows the hatch coding of the fold sequence process.

Graphics

In some embodiments, graphics are printed onto the paper substrate 334 prior to cutting, scoring and gluing the paper substrate. In some embodiments, the creasing/folding, cutting and gluing can be done very quickly through automation on digital die cutters. FIGS. 13A, 14A, and 15A illustrate the output from a printer showing the graphic areas on the paper substrate. The customer may select predetermined graphic print options or may also request customized graphic prints.

Blunt Edges

In some embodiments, the production process uses a fold pattern which employs a hidden cut method to conceal the raw cut edges in the paper substrate material 347, thereby avoiding sharp edges, allowing soft contact between the user and the chair components when folded/assembled. This may facilitate active use of the chair without the user having to take undue precaution to avoid contact with sharp edges.

Assembled Parts

FIGS. 18A, 19A, 20A, 21A, 22A, and 23A show top views of example embodiments of the seat 301, legs 302, base 303, pulp 305, electrical module 306, and counterweight mass 307 respectively. FIGS. 18B, 19B, 20B, 21B, 22B, and 23B show side views of the seat 301, legs 302, base 303, pulp 305, electrical module 306, and counterweight mass 307 respectively. FIGS. 18C, 19C, 20C, 21C, 22C, and 23C show a different side view of the seat 301, legs 302, base 303, pulp 305, electrical module 306, and counterweight mass 307 respectively. FIGS. 18D, 19D, 20D, 21D, 22D, and 23D provide perspective views of the seat 301, legs 302, base 303, pulp 305, electrical module 306, and counterweight mass 307 respectively.

Joined Parts

After folding, the various components of the chair are joined together comprising the seat 301, legs 302 and base 303 and the next cast parts 305, 307 can be built.

Elements

In some embodiments, using separated pieces provides the opportunity to use knife plate joints. For example, the vertical leg pieces may extend past the horizontal members into the cast pulp or concrete volumes in order to strengthen their bonds. Without using this method, the joint between horizontal and vertical members would be significantly weaker and would limit the applicability of using paper substrates. According to some embodiments, the methods described herein may provide an efficient way to fold up building material (e.g. paper substrate), expose no cuts 342, 347, and build up mass on the outer edge cavity 340 in a way that is efficient for the moment of inertia of the overall product (e.g. chair). In some embodiments, the joining of folded elements together is facilitated by producing male 348 & 349 and female 345 & 346 ends on the paper (for example, the leg may serve as the female end while the base has the male ends of the joint).

Paper Tube

In some embodiments, horizontal members 132 may also include a paper tube beam condition to transfer loads to the vertical orientation. The paper tube beam can connect directly to the vertical support using for example, a pulp-glue-filamentous mixture joint. Such a configuration is possible because the vertical supports leave an opening into the horizontal tubes 341. This in turn functions to efficiently translate a horizontal member support condition into a vertical support condition.

Cast Elements

Horizontal spanning elements 132 at the top are then connected to legs by filling the pipe forms with, for example, a pulp-glue-filamentous mixture. A slip-resistant base (as shown, for example, in FIGS. 23A-23D at the base of each of chairs) may comprise, for example, rubber as a casting material. The counterweight base mass 134 may contain, for example, embedded slag or lead for added weight. Finally, the seat top is covered with a cushion 130 containing, for example, high-density foam. The slip-resistant base allows for better grip between the base and the floor when the chair is subjected to extreme tilting angles (otherwise horizontal translation may result).

Connect

The term "connected" or "coupled to" may include both direct coupling (in which two elements that are coupled to each other contact each other directly) and indirect coupling (in which at least one additional element is located between the two elements).

200s (Movement)

Movement

Figure 12:
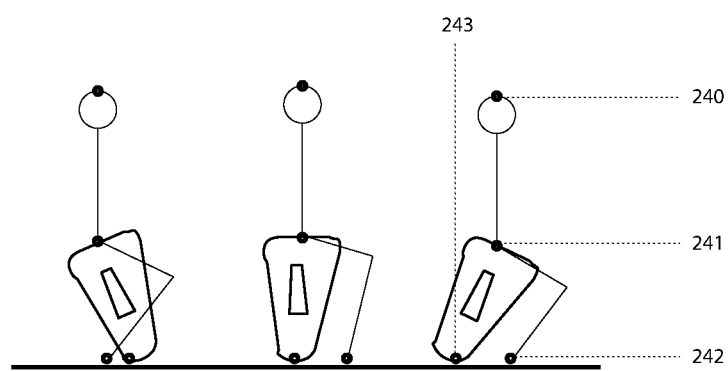
FIG. 12 shows side views of the chair in motion with the body position compensating to keep a center of balance in line.
Figure 13:
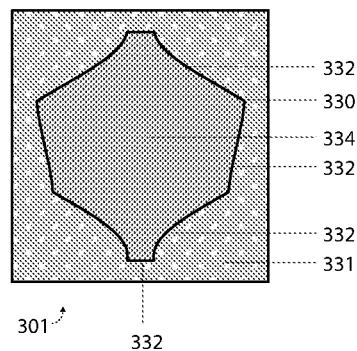
FIGS. 13A-13E illustrates overhead views of the initially produced flat forms and how they are used to transform paper tubes into example embodiments of chair seat components with exposed graphics.
Figure 13:
Figure 13:
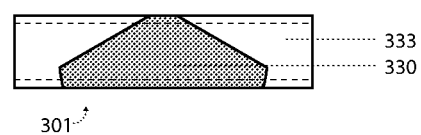
Figure 13:
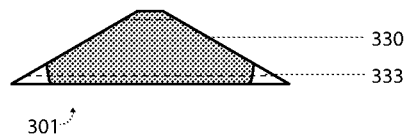
Figure 13:
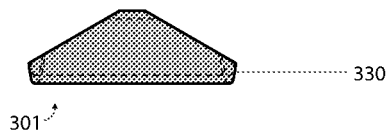
Figure 14:
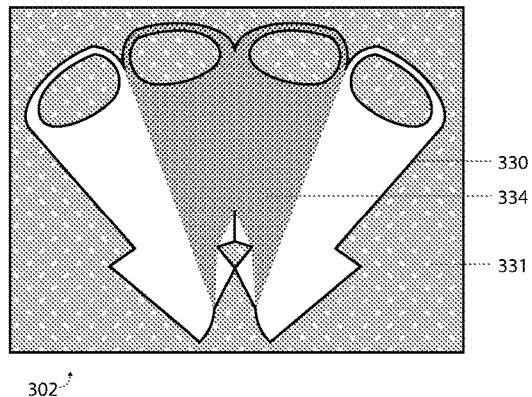
FIGS. 14A-14F illustrates overhead views of the initially produced flat forms with fold lines and how they are transformed into example embodiments of chair leg components with exposed graphics.
Figure 14:
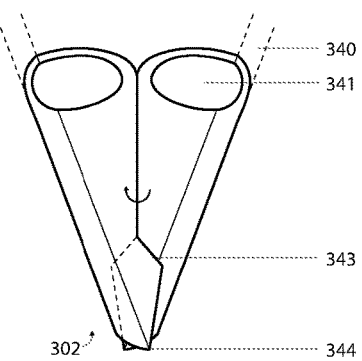
Figure 14:
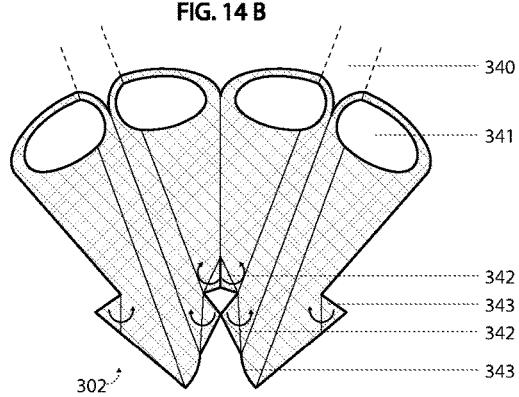
Figure 14:
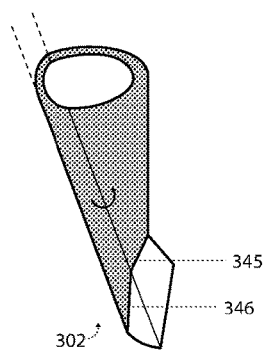
Figure 14:
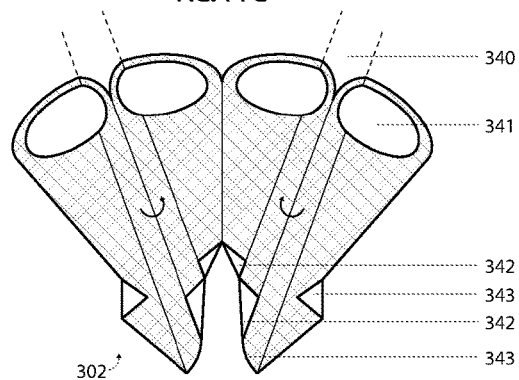
Figure 14:
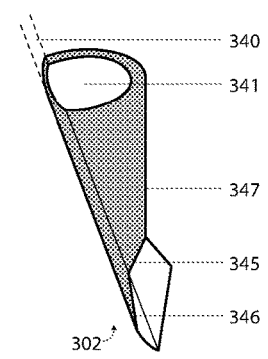

The chair is configured for dynamic seating with a capacity for rotation 236 around a central smooth point 137 and leaning around the anti-slip spherical base 134. This configuration is usable on uneven surfaces with a fluid range of motion. As shown in FIG. 12, movement of the hips 241 and head 240 are coordinated with the base of chair 243 and feet 242 to maintain a stable center of gravity.

Self-Recovery

Figure 10:
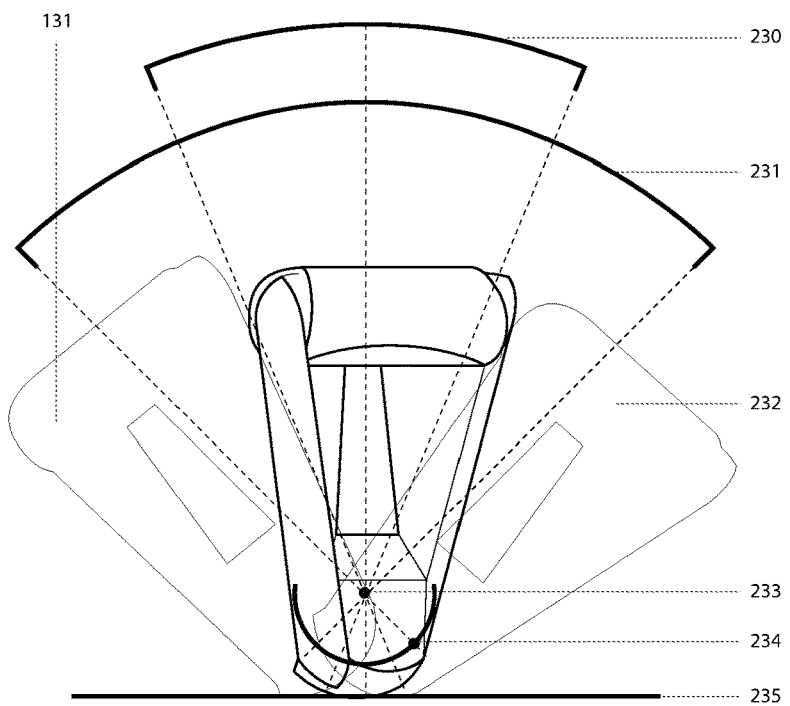
FIGS. 10 and 11 show a side and top view of an embodiment of the chair in which suitable ranges for tilting relative to a horizontal axis are compared to the necessary density of the counterweight in order to allow for self-recovery.
Figure 11:
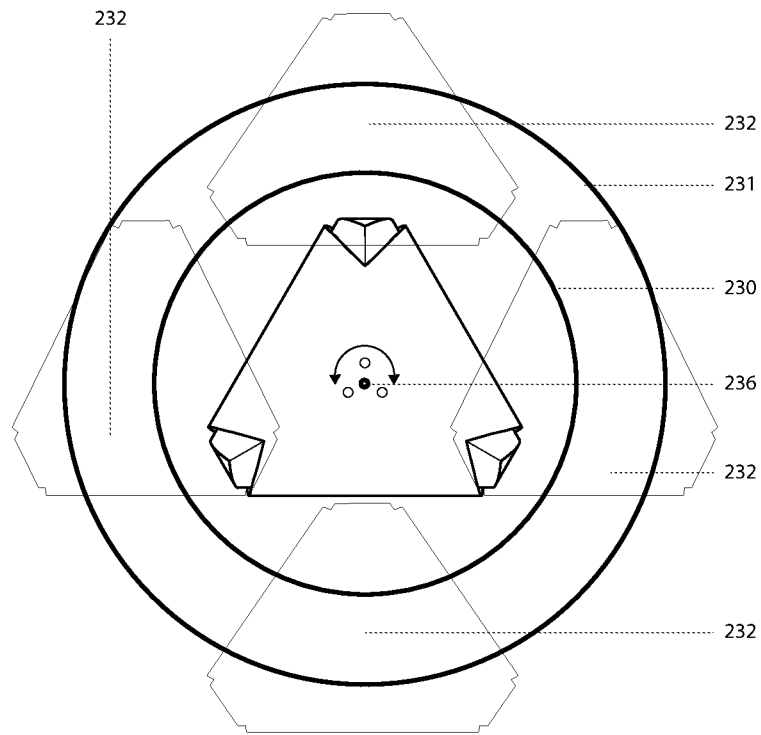

The counterweight 134 facilitates self-recovery for the chair when not being sat on by the user. FIGS. 10 and 11 show a side and top view of an embodiment of the chair 100 in which suitable ranges for tilting relative to a horizontal axis 235 are compared to the density of the counterweight 234 required in order to allow for self-recovery 231. As can be seen, some embodiments of the chair 232 can allow for quite extreme tilting angles 231, including 45 degrees or more. The degree to which the chair 100 can tilt while still allowing for self-recovery depends on the density of the counterweight 234 relative to a point of rotation 233 in the base 134. Typically, the anticipated range of motion 230 for seated use of the chair 100 is less than 45 degrees, as shown in FIGS. 10 and 11.

Paper & Curvature

In some embodiments, the lightness in mass of the upper portion due to the use of paper substrate allows for the use of a sharper curvature in the rounded or spherical shape at the base 134. This may allow the chair to recover from more extreme tilted positions 231 with relative ease as the mass of the seat is considerably lighter relative to the base 234, as shown in FIGS. 10-11. This sharper curvature is important for providing and allowing for a greater variation in range of motion and movement for the user. Other designs known in the art have a shallower curvature which therefore limits the active variation permitted. If such designs using heavier materials and different weight distributions were to use a similar curvature to that which is capable of being supported by some embodiments of the present invention, the designs would become heavier still, as extra mass would need to be added to the base.

Directionless

In some embodiments, the chair has no directionality due to the equilateral form, so any user can sit down on the chair from any angle, with a reduced likelihood of a first-time user making a mistake when attempting to use the chair. This may in turn reduce the likelihood of injuries associated with use of the chair, particularly for first-time user movement. Further, the directionless priority of movement may cause the core muscles of the user to be activated all around the body depending on the position assumed by the user when seated in the chair. The detailed feedback provided by some embodiments may allow users to track their habits and achieve healthier sitting and movement/activity pattern results over long-time use of the chair.

Body Implications

In some embodiments, the design priority is to offer control of the body through the user's hips while sitting on the chair. This is important in order to manipulate and maintain a vertical spine during use. The saddle shape of the seat 103 (as shown, for example, in FIG. 1) may be more form fitting and may permit a wider angle in elevation between the spine and thighs of the user, which may yield a more natural spinal curvature for the user and may also alleviate hip flexor tightness associated with typical sitting patterns (i.e. 90 degree hip alignment). The saddle shape also supports the thighs at a diagonal angle, which may be less obtrusive to blood flow and facilitate the maintenance of a greater surface area of contact between the user's body and the seat 103.

Benefits

Some embodiments of the invention may strengthen the physical body as well as enhance body awareness therefore enabling the user to self-adjust as a result of internal and external sensations. This helps to prevent repetitive muscle imbalance induced by sedentary seating environment (particularly prolonged stillness), and facilitate increased muscle activity in the user's core, back and leg muscles under gravitational loads while facilitating movement.

Acclimation

Although some embodiments of the invention may require the user to acclimate to the conscious effort required to balance when using the chair, the user may gradually learn how to unconsciously maneuver the user's hips to maintain balance. Once attained, use of the chair according to some embodiments may encourage a more dynamic lifestyle and produce improved muscle tone, flexible joints, alleviate pressure points, increase blood flow and increase metabolic rate. These factors may contribute to peak mental performance and increased productivity, since cognitive performance is tied to activity and blood circulation. As such, use of the chair according to some embodiments may cause human resource productivity to improve though active ergonomics.

500s, 800s (Tailored, Broader Applications)

Counterweight

Figure 15:
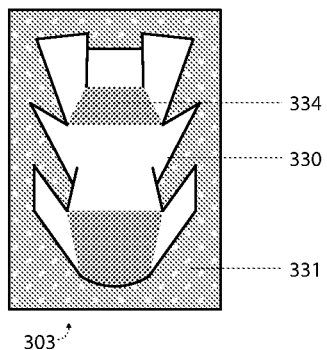
FIGS. 15A-15G illustrate overhead views of the initially produced flat forms with fold lines and how they are transformed into example embodiments of chair base components with exposed graphics.
Figure 15:
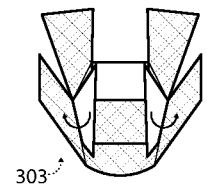
Figure 15:
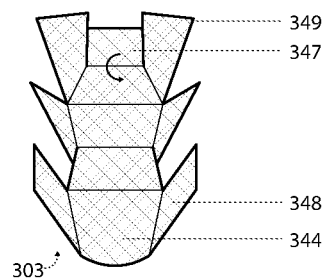
Figure 15:
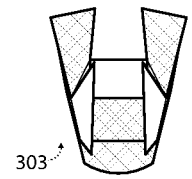
Figure 15:
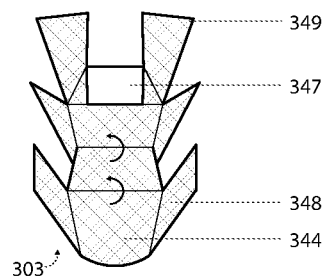
Figure 15:
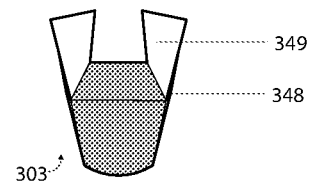
Figure 15:
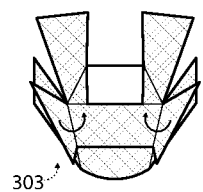
Figure 16:
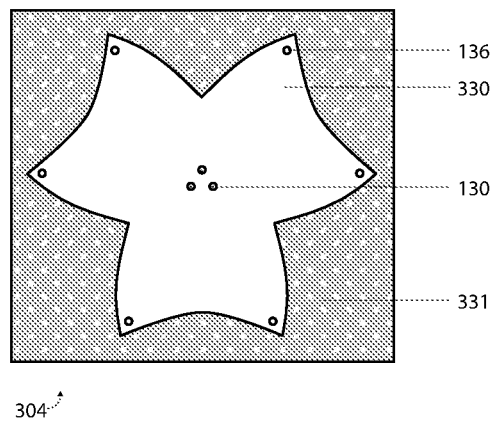
FIG. 16 illustrates an overhead view of the initially produced flat seat cover.

In some embodiments, the counterweight base formwork as shown in FIG. 15 is defined by using a flat paper edge 344 against a spherical form with adjustable placement of the dowel connections into the pulp leg elements 421. This strategy may permit the adjustment of the overall volume of the counterweight with relative ease by changing the paper boundary against a reusable spherical form. Through this method, the center of rotation for the counterweight and counterweight depth can be parametric relative to the required structure at the top seat. This strategy ensures that the counterweight spherical center can be modified independently from the volume.

Body Parameters

Figure 24:
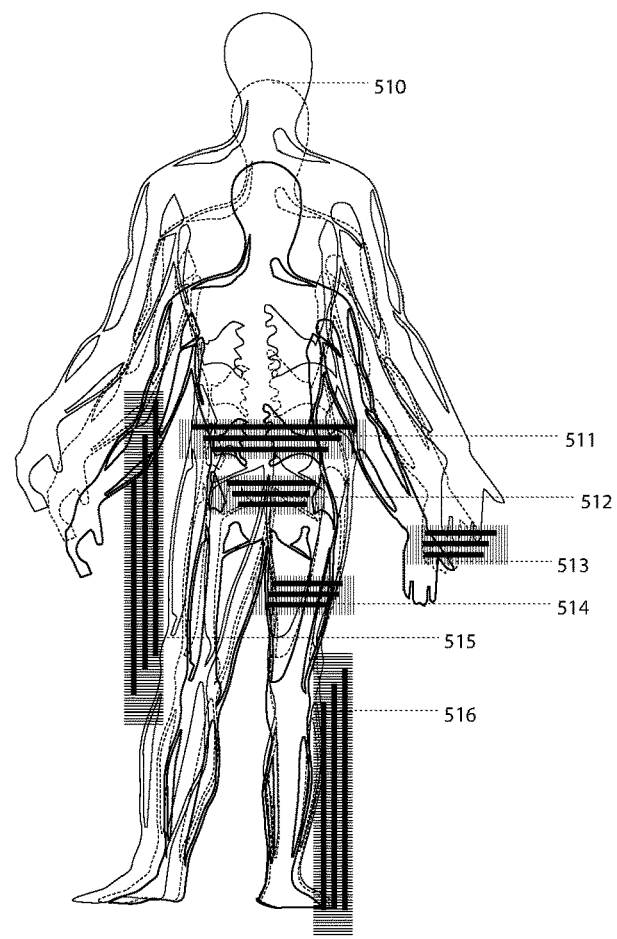
FIG. 24 shows example measurements for tailored inputs from a few different anatomical sources for generating a variety of example embodiments of the assembled components.
Figure 26A:
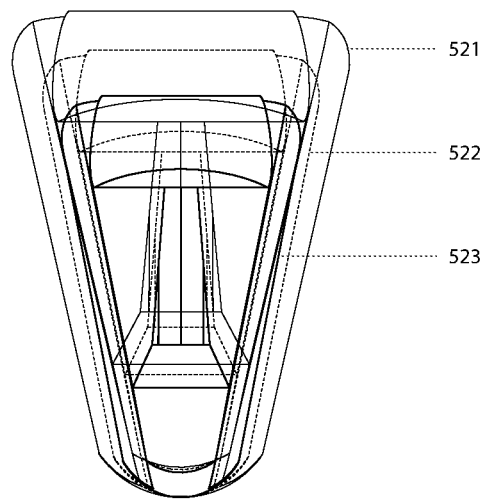
FIGS. 26A-26B show example assembled tailored output embodiments from a few different anatomical sources in back and top view.
Figure 26B:
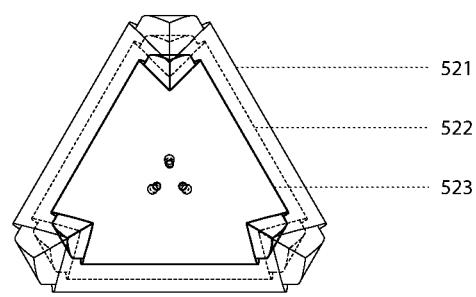
Figure 27A:
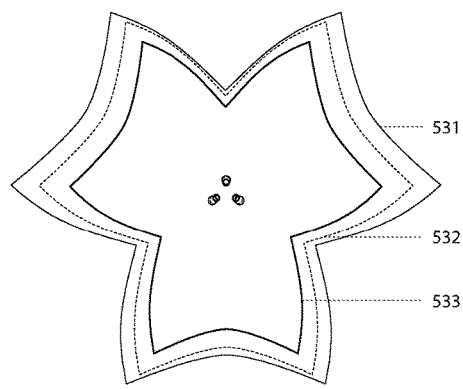
FIGS. 27A-27D illustrate overhead views of the initially produced tailored flat output embodiments from a few different anatomical sources.
Figure 27B:
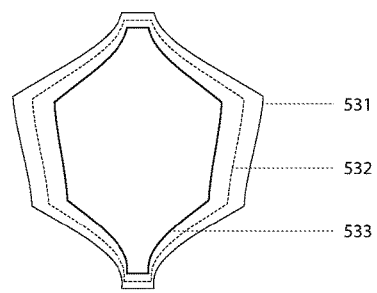
Figure 27C:
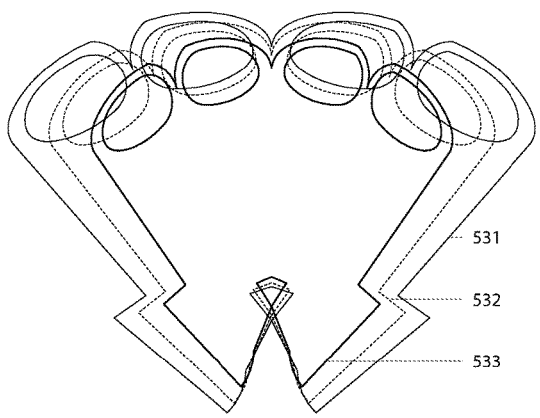
Figure 27D:
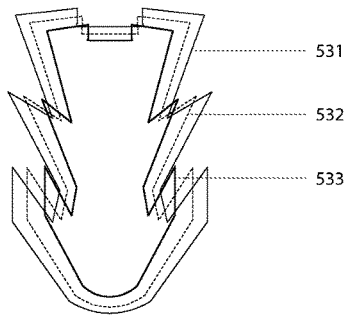
Figure 28:
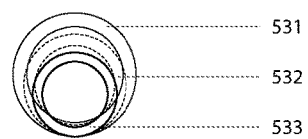
FIG. 28 illustrates a side view of the variability in paper tube diameter and/or wall thickness embodiments to meet tailored output requirements from a few different anatomical sources.

The design of the chair form is dictated by several parameters from the human body 510 shown in FIG. 24, which include for example hip width 511, seat edge curvature for thigh circulation 514, knee break height 516, inner hip width 512, conscious roll sensitivity, ventilation grip 513, and thigh length 515. Coordinating the chair design with a table height may be performed but it is preferably to prioritize for spinal alignment first. As noted above, FIG. 24 shows the values of certain parameters 511-516 and the associated body geometries. For example, a person who is taller than average may require a higher seat platform, and an individual with wider than average hips may require a wider form. FIGS. 26A-26B illustrate examples of several chairs with proportions tailored to particular users based on a variety of measurements 511-516. For example, chair 521 is based on parameters 511-516 for a user that is larger than average. Chair 522 is based on parameters 511-516 for an average user. Chair 523 is based on parameters 511-516 for a user of below average height. A person skilled in the art will appreciate that the parameter values listed in FIG. 24 are merely examples and intended to illustrate parameters that are tailored to a particular individual. Each of these parameters can also be modified independently to produce completely unique results.

Fixed Solutions

Figure 25:
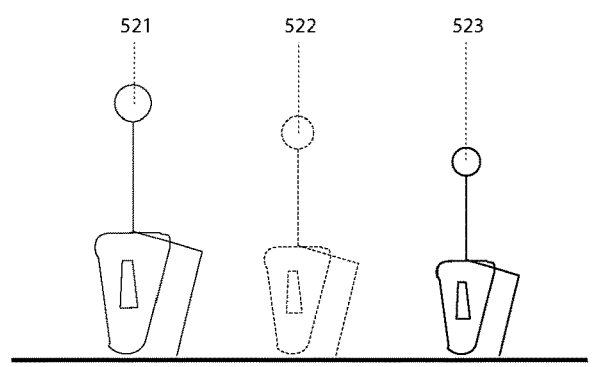
FIG. 25 shows example assembled tailored output embodiments from a few different anatomical sources in a side view and the resulting identical seated posture alignment for varying body sizes.

In some embodiments, the chair is tailored to the individual at the time of production, and does not provide for seat adjustability (e.g. dials or levers or the like for adjusting settings on the chair) during use, since optimal settings are already being provided. As such, the chair is ideally not tailored for individual table heights. Instead, the height of the desk or table at which the user is sitting may need to be adjusted to match the ideal seat height provided by the chair. In some embodiments, the chair does not include any seat adjustment knobs, as adjustment is provided through the tilting action of the chair itself. Further, according to the Canadian Centre for Occupational Health and Safety, adjustment knobs also introduce the risk that users will select settings which are improper and ultimately harmful to the user. Since the chair can be tailored to a particular user during manufacturing, the need to adjust the chair is minimal for the user, and thus associated undesirable body postures arising from potentially improper adjustments may be prevented through use of the tailored chair without altering its configuration. As illustrated in FIG. 25, the tailored outputs provide a comparable baseline for a consistent hip-spine-floor relationship. This feature is critical and permits the comparability of biomechanics evaluations listed below for the electronics.

Parametrics

In order to provide a customized chair which is tailored to the dimensions of an individual user, parametric design is used to generate the form of individual flat components shown in FIGS. 27A-D for various sizes 531-533, including creasing/fold lines and dimensions for the components. The various components of the chair according to some embodiments of the invention may be designed using, for example, Rhino 3D design together with the Grasshopper parametrics plugin. According to some embodiments, one or more of the various parameters are input into parametric equations, which output the definitions for outputting flat paper outlines, each with valid engineering parameters (including, for example, shape, thickness, joints, or the like). A particular advantage of this strategy is that the tailored mathematical relationships can be updated over time for tailoring precision to coordinate with the latest biomechanical research. Due to the consistent biomechanical baseline, those updates can be applied to all users.

Integrated Engineering

In some embodiments, the construction details are automatically configured to accommodate the variability in dimensions for a user. Since the parts for the chair are printed, cut, scored and glued on flat paper, the structural engineering is automatically integrated into the unique folded geometry outputs of FIGS. 27A-27D. It should also be noted that generically-sized components can also be developed for use in public settings where there will be more than one user and tailoring to a group demographic is desirable.

Production Automation

Due to the intrinsically tied nature of computer designs and the digital die cutting equipment, in some embodiments, the generation of the initial design on flat paper automatically responds to variations in parameters to alter the shapes of the components during production. The single parametric algorithm for the design of the chair components can structurally analyze the engineering needs in a fluid and automated manner to meet all bodily requirements of the user. At the same time, the digital die cutting equipment can work in tandem with the algorithm to produce and execute the necessary cut/score/glue patterns for automated production. This ease in customizability may lead to a very efficient, context-driven product with inherent environmental and economic benefits, since waste tends to be reduced or minimized according to some embodiments of the invention when precisely built.

Imitated Construction

After the cutting, scoring and gluing, the paper substrate is then manually folded, jointed (as described below), coated and cast. The folded paper substrate ultimately defines the structural form of the chair. In some embodiments, the folding process varies only slightly for the builder. Thus, customization for tailored chair dimensions may be achieved with minimal impact or variation on the manufacturing process.

Fluid Sizes

In some embodiments, the paper/pulp or other cast material combination allows for the fulfilling of tailoring requirements because it facilitates a number of proportions in both shape, strength and counterweight ratios to support the anticipated loads according to output sizes 531-533. No single-size structural member would be able to efficiently accomplish this result. FIGS. 28-31 illustrate how the tube diameter, tube wall thickness, pulp mass, counterweight mass structure are coordinated with the folded form. The contour of the tensile cover maintains smooth flat surface over the rounded shape thereby facilitating the use of a flat material in such geometrical conditions. The electronic module is one of the components that is built without a fluid change 534 in dimension as tailoring it does not directly offer advantages for the body.

Y Shape

Figure 29:
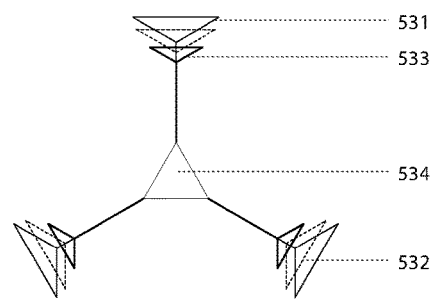
FIG. 29 illustrates a top view of the variability in cast pulp legs cross sectional area embodiments to meet tailored output requirements from a few different anatomical sources.
Figure 30:
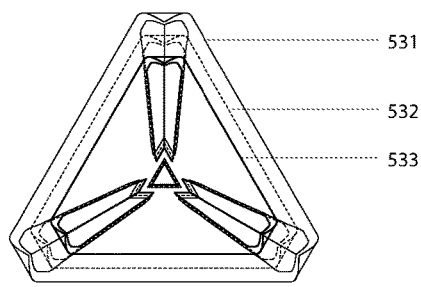
FIG. 30 illustrates a top view of the variability in cast pulp volume connection to tube embodiments to meet tailored output requirements from a few different anatomical sources.
Figure 31:
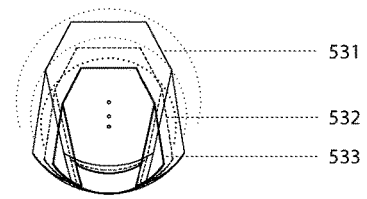
FIG. 31 illustrates a rear view of the variability in cast counterweight volume embodiments to meet tailored output requirements from a few different anatomical sources.

Furthermore, in some embodiments, the vertical leg pieces may branch apart at the outer edge in the shape of a 'Y' as illustrated in FIG. 29. This further reinforces the benefits of the moment of inertia of the chair and also provides access for joining paper tubes to cast legs with a solid form, which avoids unnecessary complexity in the construction process. In some embodiments, as shown in FIG. 47, each discrete element can by itself be folded into the shape of a product in such a way that it allows for a variety of fillers or castable materials 850 to be cast into it (e.g. pulp, concrete, insulation, or the like). In some embodiments, casting into the 'Y' shape was focused on, as the 'Y' shape is achieved by the division of legs into three sections, which is the simplest way to build up adjustable mass through adjoining flats with particulate or filamentous material, and the 3 divisions for the 'Y' shape are the fewest number of divisions by which this result can be obtained.

Coatings

The folded paper is then coated with a cellulose product (for example, cellulose nanocrystalline (CNC), described below) to add strength and a waterproof layer. In some embodiments, the structural coating is another paper substrate, but as FIG. 47 illustrates, this coating 851 can be varied according to the structural requirements. CNC comes from the cell walls of trees. Such a coating may increase the strength and stiffness of the other materials. Some embodiments of the chair will offer an efficient structural and economic balance between stock paper thickness in conjunction with CNC thickness in order to arrive at a high "green quotient".

Pulp Fill

The components of the chair according to some embodiments have a paper structural form that is defined by folds. The paper is then coated with a CNC mixture to provide appropriate strength and waterproof properties. Then solid spanning elements may be produced by filling the folded forms 340 & 344 and paper tube end 411 with a variety of mixtures 850 including a pulp-glue mixture using cellulosic fibre-reinforced filaments (CF) to increase strength. Such a combination may facilitate the unique parametric tailored generation of forms for ergonomic needs as the formwork shape is tailored 420.

Lossless

Further, using wood framing (or concrete formwork) and milling the members down to their appropriate size or discarding the formwork generates material waste. According to some embodiments of the present invention shown in FIGS. 13A, 14A, and 15A, starting from a flat product allows the remainder of the paper 331 to be mulched and used for other steps in the process. In some embodiments, 100% of the material may be consumed in producing the chair. Furthermore, the material is renewable and recyclable, high functioning and environmentally friendly. According to some embodiments, the combination of parametric, tailored designs with the use of flat paper may result in a wasteless production method which is applicable to variable forms. Such a process may also provide additional demand for local forestry industries and prevent the closing down of mills.

Seed Scale

A person skilled in the art will appreciate that this parametric seed logic imitates the way a tree can grow into a multitude of final outputs based on contextual pressures from just a simple seed. The parametric seed logic described herein may be developed and applied to other products, even those which do not use paper substrate technology, and for applications which are larger or smaller than chairs 800 such as a table 801, frame 802 or complete enclosure 803. Such technology may be applied, for example, to building components illustrated in FIG. 42. As such, a person skilled in the art will appreciate that the seed strategy can be applied to other products including the support of heavier loads in the built environment and on an increasing scale. By having separated the horizontal and vertical elements into discrete parts that can be prepared independently, the value of the construction method may be increased substantially to larger scales than a chair. Although infinitely large paper cannot be sourced, and joints would be required for increasingly larger scale objects, a benefit derived from separating parts into discrete objects is that the production strategy does not have to be redefined for products which increase in size. If the chair were to have been made of one piece of material, the production strategy may need to be redefined for larger objects. As such, some embodiments of the construction strategy disclosed herein are highly scalable as shown in FIG. 42. The construction strategies which may make assembly easier are the tailored framework, folded joints, and simplified casting, all of which can be controlled and managed digitally, which may allow for the customizability and variations on the end product 804 and have minimal to no impact on the construction process. In particular, the cast folded Y-shape 805 scales proportionately to the scale of the built object and also integrates the single or double ended outputs. Male and female connections 806 are also alternated according to each element.

Scale Materials & Shapes

There are a number of advantages which may be realized by some embodiments of the invention over alternative methods. For example, 3D printers still suffer from limitations in terms of the size of objects that can be produced accurately, and face many problems when attempts are made to join 3D prints together to achieve larger volumes. Even at the scale of a chair, 3D printing is difficult. According to some embodiments of the present invention, using reinforced folded paper for joints allows for the joints to provide registration for proper alignment and defines the profile for the curved formwork. Further, unlike 3D printing, the production speed for some embodiments of the processes described herein can be quite fast, as the cutting, creasing and folding are processes that are amenable to use with a material with strong bonds between cellulose fibres. Contrastingly, 3D printing requires the build-up of chemical connections between each particle. While this affords potentially more flexibility in the final output shape, 3D printing tends to be limited in its capacity for speed and size relative to some embodiments of the processes described herein. As noted above, the processes described herein are scalable. For example, FIG. 43 shows an example embodiment in which additional members 810 are added for different geometrical configurations 811, and how these members can be scaled in terms of both length and the proportion of paper to pulp. FIG. 44 also illustrates how the response to moment of inertia can be tailored by increasing to double-ended masses 820 as the distance 821 between frames expands out away from a smaller center 822 where single-ended masses 823 were appropriate. FIG. 46 shows how these ends can be independently sizable ends 840, 841. This invention also permits a wider range of material variability than 3D printing as the solid forms can be cast afterwards like a typical construction process so a wider variation in the filler 850 and coating material 851 are acceptable. As shown in FIG. 45, the flat paper stock 830 can be replaced with, for example, a metallic material further increasing the applicability for the architectural scale. Both these materials are available in roll form 831, further supporting longer spanning distances.

Combinations

The preceding disclosure has provided many example embodiments. Although each embodiment represents a single combination of inventive elements, other examples may include all possible combinations of the disclosed elements. Thus, if one embodiment comprises elements A, B and C, and a second embodiment comprises elements B and D, other remaining combinations of A, B, C or D may also be used.

Variation

Although example embodiments have been described in detail, it should be understood that various changes, substitutions and alterations can be made herein without departing form the scope as defined by the appended claims. Mathematical relationships that define the precise geometries can also be updated over time to coordinate with tailored, structural or movement requirements.

600s, 700s (Electronics, User Interface)

Physical Description

The electronic housing is connected to the folded knife plate 343 inside the counterweight mass. This space is a void 440 that is filled with the electronics module depending on the customer. An electronic module can indicate battery life with a light visible on the exterior and charge the battery using a removable plug from the top 430. During installation of the electronic module, a triangular form with a 3 point corner balance adjustment is used to set the accelerometer correctly to a level ground surface. This module may assist in increasing the dynamic functions of the chair.

Basic Functions

Figure 1:
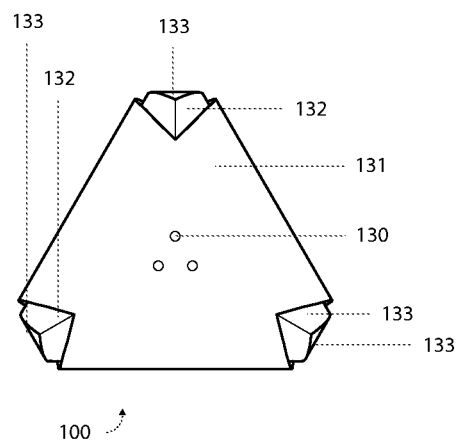
FIGS. 1-7 illustrate a top, bottom, back, right, front, left, perspective view respectively of components of an example embodiment of an assembled chair according to the invention.
Figure 2:
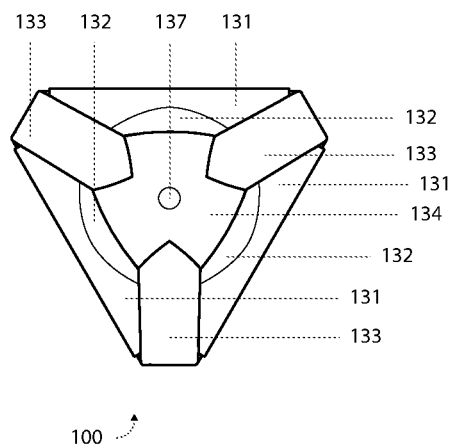
Figure 3:
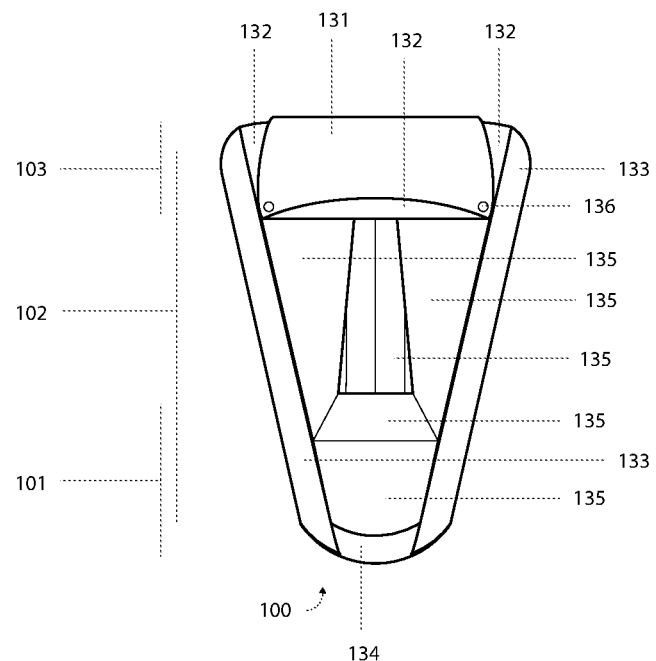
Figure 4:
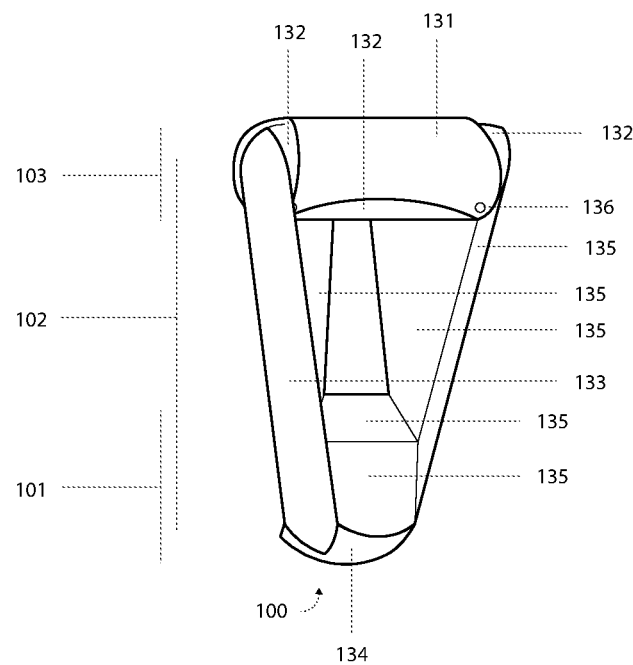
Figure 5:
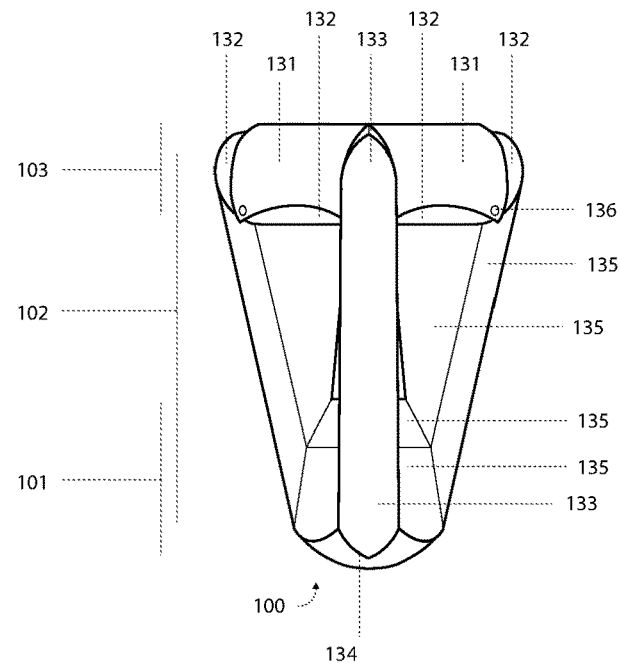
Figure 6:
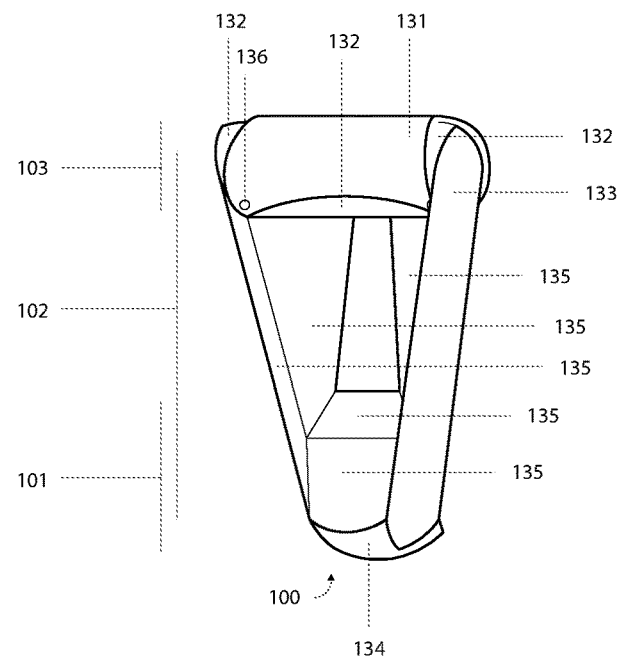
Figure 7:
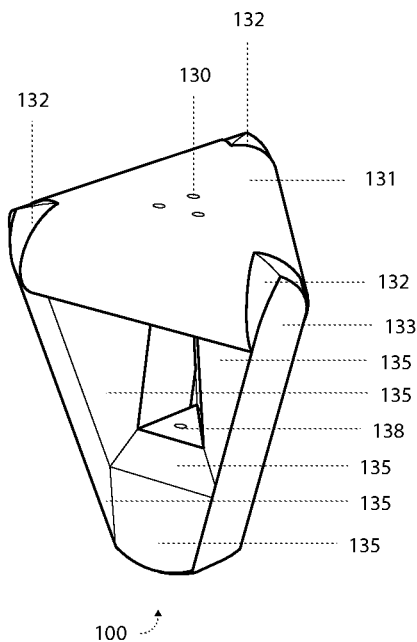
Figure 8:
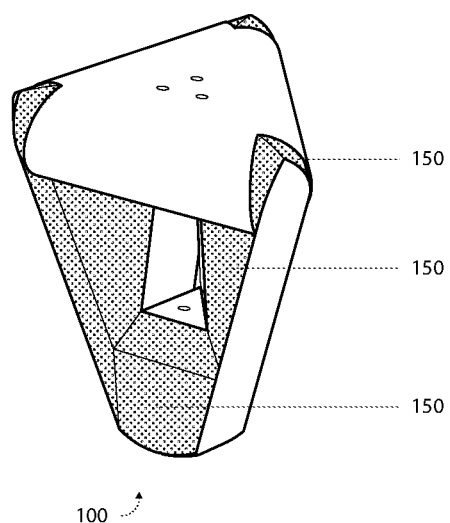
FIG. 8 shows a perspective view of the graphic components of an example embodiment of a chair according to the invention.
Figure 9:
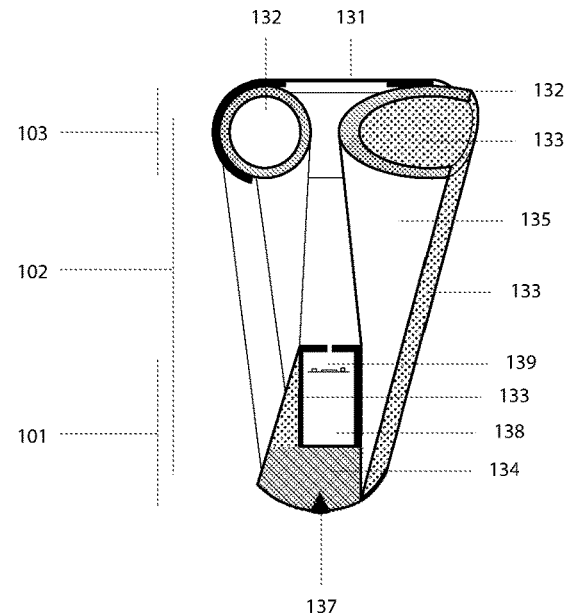
FIG. 9 shows a section view of components of an example embodiment of a chair according to the invention.
Figure 32:
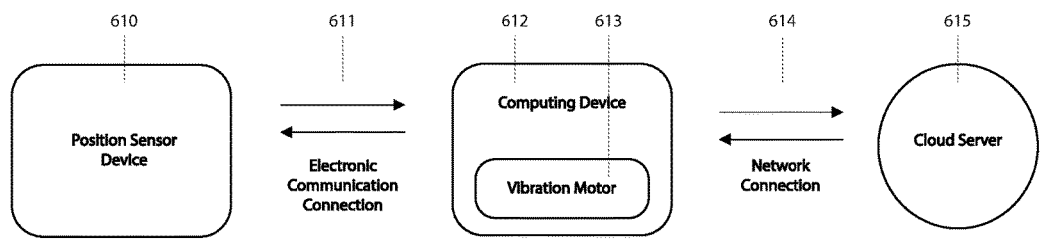
FIG. 32 schematically illustrates a system having a position sensor device that sends acceleration data for the x, y, and z axes to a connected computing device configured to interpret the x, y, and z acceleration data and to determine position of the user sitting on the chair using the earth's gravity vector, in the z-axis, as a reference. Feedback from the computing device may be given to the user in order to correct position and maintain ergonomic or proper biomechanical positioning. Communication from the computing device to the position sensor device may be used for configuration, testing, and calibration. In some embodiments, applications do not require a cloud server, but in other embodiments, the applications involve a data link between the computing device software and the cloud server.
Figure 37:
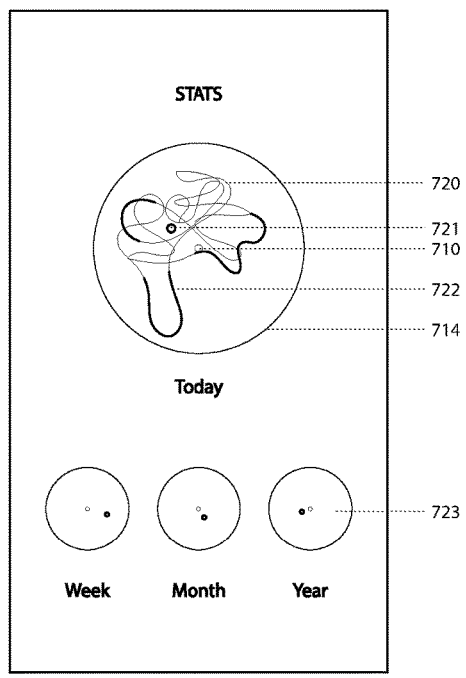

In some embodiments, as shown by way of example in FIG. 9, the counterweight 134 in the base 101 of the chair 100 comprises an accelerometer 139 inside of a housing 138. In some embodiments, there is only a single accelerometer embedded in the chair, i.e. no other sensors are embedded in the chair. The accelerometer 139 may be powered any number of ways, for example by a battery 638, which may be rechargeable via the DC power port 636. The accelerometer 139 may be adapted to track the posture of the user when seated, and can provide live and historical feedback as shown in FIG. 37. In some embodiments, the accelerometer 139 is capable of detecting movement variations of as little as 1 degree, in order to distinguish subtle changes to a user's seating position 720. An example showing the functions of the single accelerometer are shown in FIG. 32, which illustrates a position sensor device interpreting the gravitational forces 610 and communicating 611 with a computing device 612. This computing device tracks the received data 612, can then interpret and relay messages or signals to a vibration motor 613 or a cloud server 615 through a network connection 614, and run an application (or "app") programmed to receive and record ("track") the received data. The position sensor device 610 of FIG. 32 may in one embodiment be mounted on a position sensor circuit board 631 and may include the components illustrated in FIG. 33. The physical layout of the position sensor circuit board 631 is illustrated in detail in FIG. 33 where the accelerometer (i.e. the IMU device) 632 generates and transmits position data 633 to the microprocessor 634. This position data may be received and processed ("interpreted") by the microprocessor 634 to determine whether a corrective action or user notification is required. If an action or notification is required, the microprocessor then generates and transmits a drive signal to the vibration motor and drive circuit 637 and/or transmits a message or signal to the wireless communication device 635. The position sensor circuit board 631 may be powered with the DC power port 636 and battery and charging system 638. The accelerometer that is used as the IMU device 632 may be piezoelectric, piezoresistive or capacitive.

Activation

When the chair is not in use it will wait a set amount of time and then go into sleep mode to conserve battery power. "Not in use" will be termed as no significant movement and having an approximate tilt correlating to the resting position of the chair. According to FIG. 34, once the chair is moved a significant amount 651 and the tilt is changed 653, the Bluetooth® module 652 in the chair will attempt to establish a wireless data connection 654 with the computing device 655, i.e. a central processing device which may be a phone, watch, tablet, laptop computer or desktop computer. If pairing is achieved and movement and/or active tilt is maintained, the module will function normally. If pairing is not achieved, i.e. the computing device 655 is not in the vicinity, the Bluetooth® module 652 will make a set number of re-attempts at pairing. If these are unsuccessful the chair module will revert to sleep mode. The computing device 655 may run, for example, the Android® operating system, the iOS operating system, the Windows® Phone operating system, or any other acceptable operating system that supports the use of, for example, Bluetooth® communication networks. In some embodiments, the application sends a notification to the user to indicate that login and measurement of data has been initiated.

Cloud

In some embodiments, the recorded data can also be transmitted to a central server 615 having a memory and a processor coupled to the memory to store and process the recorded data. In some embodiments, the data may also be transmitted to a central database for further processing, study or statistical analysis. This may require permission of the user. Such information sharing may result in the compiling of records for individual users, which can be contrasted to the individual biomechanics results that illustrate spinal alignment according to the seat axis (see, for example, the images of a user's posture in FIG. 11B). This data can, in turn, be used to refine the parametric equations used to provide further refinements to the tailored chair based on the performance of the users.

In accordance with another aspect of the present invention, an application ("app") is provided in the form of a computer-readable medium comprising computer-readable instructions in code which, when stored in a memory of the computing device 655 and executed by a processor of the computing device 655, cause the computing device 655 to perform various actions or operations and/or to process data and/or to display results and/or to transmit other data. Some of the functions and features of this application are depicted with reference to the graphical user interfaces shown in FIGS. 35-41.

Login

Figure 35:
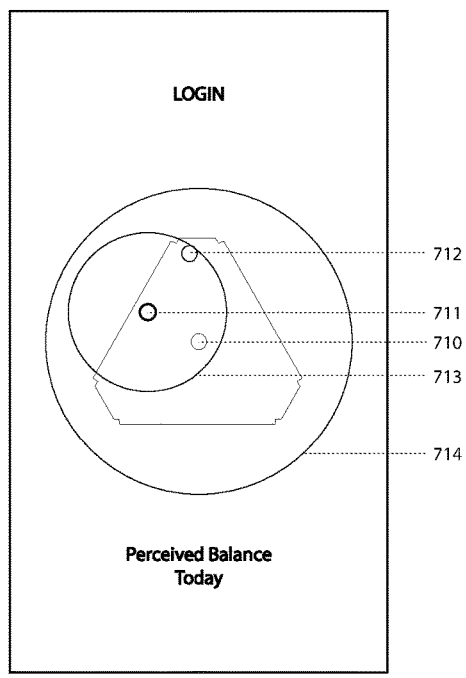
Figure 36:
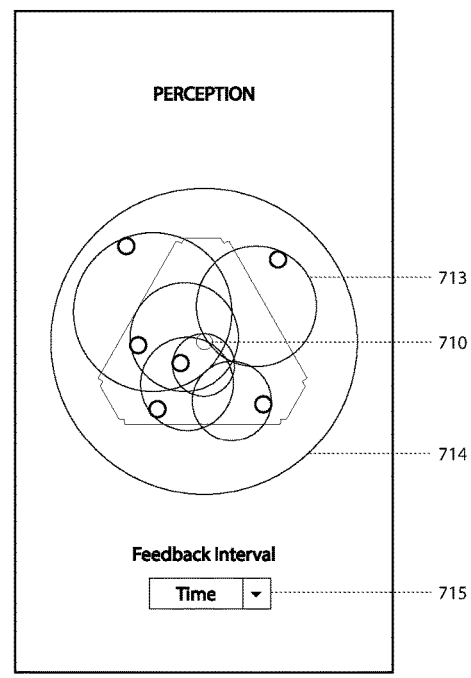

As shown in FIG. 35, periodically at the login interface the user is presented with a diagram of the chair with a neutral balance 710 within a total range of motion 714. The user may submit their perceived average balance 711 and may subsequently be presented with the actual average balance 712. These two points can then be compared to show the perceived difference 713. In practice, this feedback will support self-monitoring, which will increase self-awareness and lead to self-management where the user can transfer gained knowledge to diverse contexts (sitting or any other activity that takes posture into consideration) with or without the use of the app. FIG. 36 shows an interface that presents a summary of multiple perception results 713 according to a total period of time chosen 715 so that perception predispositions can be identified.

Position & Depth Feedback

Figure 38:
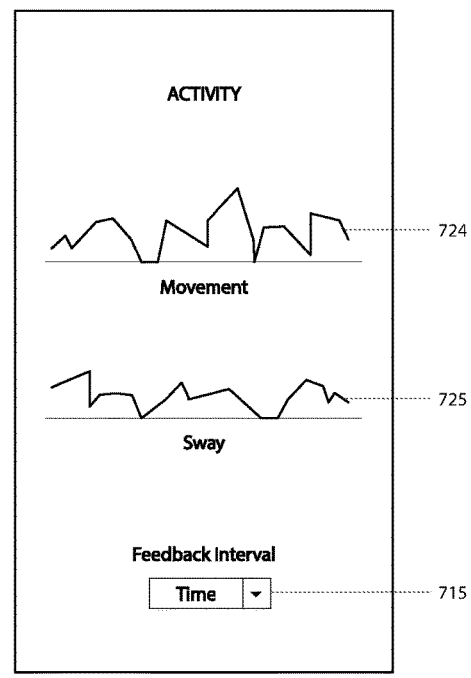

As shown in FIGS. 37-38, the application running on the computing device 655 may receive data from the accelerometer via a wireless transceiver such as a Bluetooth® transceiver providing a short-range wireless connection to track and display the posture of the user and record the user's alignment 720. The application may instruct the computing device to display live data 720-722 or historical data 723 via a graphical user interface as shown by way of example in FIG. 37. The application may be specifically customized or configured to a particular user, although any user could download the application to their phone for use with any chair according to some embodiments of the invention. This would be useful particularly in the case of chairs which are designed with generic dimensions and not tailored for a particular user. A customized summary for an individual user could thus be provided on the basis of their computing device having the application installed and registered. The application described above comprises computer-readable code or instructions that are stored on a non-transitory computer readable medium such as the memory of the computing device 655 or any other suitable wireless-enabled device. The computing device 655 includes a processor coupled to the memory for executing the code of the application to cause a display screen of the computing device 655 to present or render the various interfaces shown in FIGS. 35-41.

Activity Feedback

The application may also record the angle of tilt or inclination from the vertical gravitational axis 720 and the duration spent at each angle 722. Such data may yield evidence of a persistent predisposition for a user to sit in a given tilt direction 721, which can then be reported to the user via a user interface as shown in FIG. 38 and thus potentially result in corrective action by the user through vibration feedback. The position data may also be summarized into a record of movement 724 as well as sway 725 over an adjustable timeframe 715.

Muscle Activity & Joint Alignment

Figure 39:
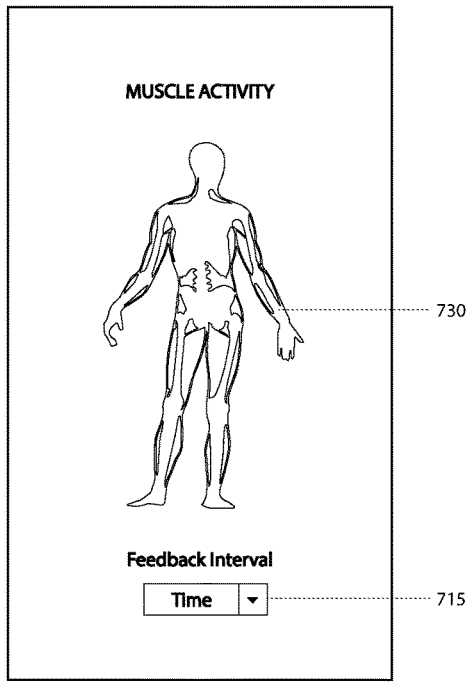
Figure 40:
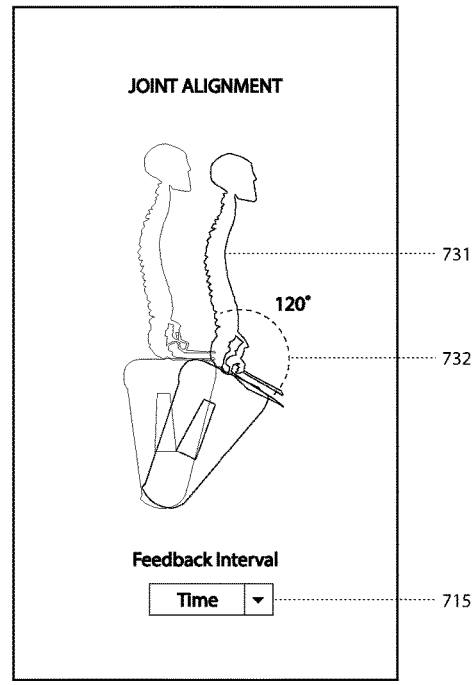

Due to the tailored biomechanical baseline, recorded movement 720-722 can be translated into muscle activity and joint alignment. In FIGS. 39 and 40, the results of muscle activation 730, joint alignment 731 and joint angle 732 are shown according to an adjustable timeframe 715.

FIG. 39 depicts an interface showing muscle activity. FIG. 40 depicts an interface showing joint alignment.

Vibration

With reference to the interface presented in FIG. 41, the results of recorded movement 720-722 can be converted or translated into vibration notifications relating to corrections in position, speed, duration, and the static/dynamic ratio. The user's movement patterns may be analyzed and translated into either a static or moving recommended seat tilt location 740. Then a spectrum of vibration intensity radiates out from this recommended destination to urge or encourage the user to move to a precise point where no vibration can be felt. This method supports positional changes to a range of available positions on the chair while remaining hands free. These hot-cold recommendations may also be in response to an adjustable timeframe 715.

Compatibility

Since the accelerometer may be built into the counterweight base 101, this may allow for additional computing device 655 or computer applications to be developed by third party users. For example, fitness regimens can be developed to alert the user that the user should change position, or change the user's tilt direction. Alternatively, the tilting action of the user could be detected and used by an application to take action, for example, to control the playing of music from the smartphone, or controlling the lighting in the room. The use of the accelerometer may also provide an opportunity to conduct biomechanical research and develop a progressively improved set of parametric equations for healthy, active posture.

It is to be understood that the singular forms "a", "an" and "the" include plural referents unless the context clearly dictates otherwise. Thus, for example, reference to "a device" includes reference to one or more of such devices, i.e. that there is at least one device. The terms "comprising", "having", "including", "entailing" and "containing", or verb tense variants thereof, are to be construed as open-ended terms (i.e., meaning "including, but not limited to,") unless otherwise noted. All methods described herein can be performed in any suitable order unless otherwise indicated herein or otherwise clearly contradicted by context. The use of examples or exemplary language (e.g. "such as") is intended merely to better illustrate or describe embodiments of the invention and is not intended to limit the scope of the invention unless otherwise claimed.

While several embodiments have been provided in the present disclosure, it should be understood that the disclosed systems and methods might be embodied in many other specific forms without departing from the scope of the present disclosure. The present examples are to be considered as illustrative and not restrictive, and the intention is not to be limited to the details given herein. For example, the various elements or components may be combined or integrated in another system or certain features may be omitted, or not implemented.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the inventive concept(s) disclosed herein.

The invention claimed is:

1. A chair comprising:
  a base including a counterweight;
  a seat connected to the base and supported above the base by a seat-supporting structure, and
  wherein each of the base, the seat and the seat-supporting structure are made at least in part of folded paper substrate material that forms at least one cavity that includes a castable material within the cavity.

2. The chair of claim 1 further comprising:
  a single accelerometer for providing position data;
  a wireless transceiver for communicating wirelessly with a computing device and for transmitting the position data to the computing device.

3. The chair of claim 2 further comprising a vibration motor for generating vibrations as feedback to a user.

4. The chair of claim 1 wherein the folded paper substrate material is coated with a cellulose nanocrystalline (CNC) coating.

5. The chair of claim 1 wherein the folded paper substrate material comprises printed graphics.

6. The chair of claim 1 wherein the seat-supporting structure comprises a plurality of legs that include a paper substrate mass.

7. The chair of claim 1 wherein the castable material forms the counterweight.

8. The chair of claim 1 wherein the castable material defines a paper substrate mass.

9. The chair of claim 8 wherein the paper substrate mass is formed of a pulp-glue mixture.

10. The chair of claim 9 wherein the pulp-glue mixture contains cellulosic fibre-reinforced filaments.

11. The chair of claim 10 wherein the accelerometer is on a position sensor circuit board that also includes a microprocessor to determine if corrective action or user notification is required based on position data obtained by the accelerometer.

12. The chair of claim 11 wherein the position sensor circuit board is within the base.

13. The chair of claim 1 wherein the chair has dimensions tailored to a user.

14. The chair of claim 1 wherein the paper substrate material is folded to conceal raw cut edges.

15. The chair of claim 1 wherein the paper substrate material are folded to form male and female joints.

* * * * *